US006258856B1

(12) United States Patent
Chamberlain et al.

(10) Patent No.: US 6,258,856 B1
(45) Date of Patent: Jul. 10, 2001

(54) METHOD FOR PREVENTING OR CONTROLLING CATARACT

(75) Inventors: Coral Gwenda Chamberlain, Five Dock; Johnston William McAvoy, Stanmore; Angela Maria Hales, Marrickville, all of (AU)

(73) Assignee: The University of Sydney, Sydney (AU)

( * ) Notice: Subject to any disclaimer, the term of this patent is extended or adjusted under 35 U.S.C. 154(b) by 0 days.

(21) Appl. No.: 09/331,510

(22) PCT Filed: Dec. 19, 1997

(86) PCT No.: PCT/AU97/00865

§ 371 Date: Jun. 25, 1999

§ 102(e) Date: Jun. 25, 1999

(87) PCT Pub. No.: WO98/26784

PCT Pub. Date: Jun. 25, 1998

(30) Foreign Application Priority Data

Dec. 19, 1996 (AU) .................................................. PO 4271

(51) Int. Cl.$^7$ ...................... A61K 31/565; A61K 31/365; A61K 31/105

(52) U.S. Cl. .......................... 514/912; 424/427; 424/424; 424/422; 514/730; 514/680; 514/453; 514/449; 514/312; 514/279

(58) Field of Search ..................................... 514/912, 730, 514/449, 312, 279, 453, 680; 424/427, 422

(56) References Cited

U.S. PATENT DOCUMENTS 5,405,944    4/1995    Suzuki et al. .

FOREIGN PATENT DOCUMENTS

WO 95/13827    5/1995    (WO) .
WO 96/19458    6/1996    (WO) .

OTHER PUBLICATIONS

Hales, A.M. et al. "Estrogen Protects Lenses Against Cataract Induced by TGF–β". *Journal of Experimental Medicine*, vol. 185, No. 2, 1997 (Jan. 20, 1997), pp. 273–280.
Cumming, R.G. et al. "Hormone Replacement Therapy, Reproductive Factors, and Cataract. The Blue Mountains Eye Study." *American Journal of Epidemiology*, Vo. 145, No. 3, 1997 (Feb. 1, 1997), pp. 242–249.
Klein, B.E. et al. "Is There Evidence of an Estrogen Effect on Age Related Lens Opacities? The Beaver Dam Eye Study." *Arch. Ophthalmology*, vol. 112, No. 1, pp. 85–91.
Merck Index, 12th Edition. Merck Research Laboratories, NJ, 1996, p. THER–22, listing under Estrogen.

Cernea, P., Ignat, F. and Danciulescu D. 1989. "Cataracta Pathologica Din Insuficienta Ovariana." Revista de Chirurgie, Oncologie, Radiologie, Orl, Oftalmologie, Stomatolgie–Seria: Oftmologie. 33:187–192. (Abstract).
Chan, C.C., Davis, V.L., Schoen, T., Li Q., Korach, K.S. and Chader, G.J. 1996. "The Role of Estrogen on Cataract Formation: A Study of Transgenic Mice With Mutation of Estrogen Receptor." ARVO abstract. *Invest. Opthalmol Vis Sci.* 37:S988. (Abstract).
Hales, A.M., Schulz, M.W. Chamberlain, C.G. and McAvoy, J.W. 1994. TGFβ1 Induces Lens Cells to Accumulate α–smooth muscle action, a marker for subcapsular cataracts. *Curr. Eye Res.* 13:885–890.
Hales, A.M., Chamberlain, C.G. and McAvoy, J.W. 1995. "Cataract Induction in Lenses Cultured With Transforming Growth Factor–β." *Invest. Ophthalmol. Vis. Sci.* 36:1709–1713.
Hales, A.M. Chamberlain, C.G. and McAvoy, J.W. 1996. "Induction of Subcapsular Cataract in Cultured Weaning and Adult Rat Lenses by TGFβ2." *Invest. Ophthalmol. Vis. Sci.* 37:S983. (Abstract).
Harding, J.J. 1994. "Estrogens and Cataract." *Arch Opthalmol.* 112:1511.
Herman, M.E. and Katzenellenbogan, B.S. 1994. "Alterations in Transforming Growth Factor–α and –β Production and Cell Responsiveness During the Progression of MCF–7 Human Breast Cancer Cells to Estrogenautonomous Growth." *Cancer Research* 54:5867–74.
Klein, B.E.K., Klein, R. and Linton, K.L.P. 1992. "Prevalence of Age–Related Lens Opacities in a Population. The Beaver Dam Eye Study." *Opthalmol.* 99:546–552.
Lambert, B.W. "The Effects of Progestins and Estrogens on the Permeability of the Lens." *Arch Opthal.* 1968; 80:230–234.
Liu, J., Hales, A.M., Chamberlain, C.G. and McAvoy, J.W. 1994. "Induction of Cataract–like Changes in Rat Lens Epithelial Explants by Transforming Growth Factor β." *Invest. Ophthalmol. Vis. Sc.* 35:388–401.
Livingston, P.M., Guest, C.S., Stanislavsky, Y., Lee, S., Bayley, S., Walker, C., McKean, C. and Taylor, H.R. 1994. "A Population–Based Estimate of Cataract Prevalence: The Melbourne Visual Impairment Project Experience." *Dev Ophthalmol.* 26:1–6.

(List continued on next page.)

*Primary Examiner*—Charanjit S. Aulakh
(74) *Attorney, Agent, or Firm*—Fulwider Patton Lee & Utecht, LLP

(57) ABSTRACT

A method for preventing or treating pathological changes which occur in association with cataract formation in the mammalian eye by protecting lens cells against the cataractogenic effects of transforming growth factor-β (TGFβ). Estrogen or an estrogenic substance can be administered to the mammal or directly to or near the eye of the mammal. The means of administration can be by a pharmaceutical composition comprising estrogen, a membranous ocular patch impregnated with estrogen or a lens or lens implant coated or impregnated with estrogen.

23 Claims, 8 Drawing Sheets

OTHER PUBLICATIONS

Pastorcic, M., De, A., Boyadjieve, N., Vale, W. and Sarkar, D.K.. 1995. "Reduction in the Expression and Action of Transforming Growth Factor B1 on Lactotropes During Estrogen–induced Tumorigenesis in the Anterior Pituitary." *Cancer Research* 55:4892–8.

Robinson, J.A., Riggs, B.L., Spelsberg, T.C. and Oursler, M.J. 1994. "Osteoclasts and Transforming Growth Factor–β: Estrogen–Mediated, Isoform–Specific Regulation of Production." *Endocrinology.* 137:615–621.

Scharf, J., Azzam, N., Schapira, D., Dovrat, A., Gershon, D. and Silbermann, M. 1995. "Influence of 17β–Estradiol and Progesterone on Rat Ocular Lens." *Opthalmic Res.* 27:197–201.

Schwab, I.R., Armstrong, M.A., Frienman, G.D., Wong, I.G., Carpantieri, A.C. and Dawson, C.R. "Cataract Extraction. Risk Factors in a Health Maintenance Organisation Population Under 60 Years of Age." *Arch Ophthalmol.* 1988; 106:1062–1065.

Takahashi, T., Eitzman, B., Bossert, N.L., Walmer, D., Sparrow, K., Flanders, K.C., McLachlan, J. and Nelson, K.G. 1994. "Transforming Growth Factors β1, β2 and β3 Messenger RNA and Protein Expression in Mouse Uterus and Vagina During Estrogen–Inducted Growth: A comparison to Other Estrogen–Regulated Genes." *Cell Growth & Differentiation.* 5:919–935.

Thompson, J.B., Deane, J.S., Hall, A.B. and Rosenthal, A.R. 1996. "Oestrogen and Lens Opacities in the Melton Eye Study." *Invest., Ophthalmol. Vis. Sci.* 37:S585 (Abstract).

Zhang, L., Rees, M.C.P. and Bicknell, R. 1995. "The Isolation and Long–Term Culture of Normal Human Endometrial Epithelium and Stroma." *Journal of Cell Science.* 108, 323–331.

Bisaria, K.K. 1980. "Effect of Estrogen on Lens Epithelium in the Albino Rat." *Ind. J. Physiol. Pharmac.* 24:357–360.

Black, H. 1996. "Viscoelastics Can Be Divided Into Two Groups According to Specific Characteristics." *Ocular Surgery News*, International Edition7(11):17.

Dorrington, J.H., Bendell J.J. and Khan, S.A. 1993. "Interactions Between FSH, Estradiol–17β and Transforming Growth Factor–β Regulate Growth and Differentiation in the Rat Gonad." *J. Steroid Biochem. Mol. Bio.* 44; 441–447.

Eshagian, J. 1982. "Human Posterior Subcapsular Cataracts." *Trans. Ophthal. Soc. U.K.* 102:364–368.

Green, W.R., and McDonnell, P.J. 1985. "Opacification of the Posterior Capsule." *Trans. Ophthalmol. Soc. U.K.* 104:727–739.

Griffing, G.T., and Allen, S.H. 1994. "Estrogen Replacement Therapy at Menopause." *Postgrad. Med.* 96:131–140.

Jordan, V.C., Mittal S., Gosden, B., Koch, R. and lieberman, M.E. 1985. "Structure–Activity Relationships of Estrogens." *Env. Health Perspectives.* 61, 97–110.

Kappelhof, J.P. and Vrensen, G.F.J.M. 1992. "The Pathology of After–Cataract: A Mini–Review." *Acta Ophthalmologica.* Suppl 205:13–24.

Kingsley, D.M. 1994. "The TGF–β Superfamily: New Members, New Receptors, and New Genetic Tests of Function in Different Organisms." *Genes & Development* 8:133–146.

Lobo, R.A. 1987. "Absorption and Metabolic Effects of Different Types of Estrogens and Progestogens." *Obstetrics and Gynaecology Clinics of North America.* 14(1):143–167.

Murphy, C.R., and Rogers, A.W. 1981. "Effect of Ovarian Hormones on Cell Membranes in the Rat Uterus III. The Surface Carbohydrates at the Apex of the Luminal Epithelium." *Cell Biophys.* 3:305–320.

Ni, N. and Yager, J.D. 1994. "Comitogenic Effects of Estrogens on DNA Synthesis Induced by Various Growth Factors in Cultured Female Rat Hepatocytes." *Hepatology* 19:183–92.

Raisz, L.G. 1996. "Estrogen and Bone: New Pieces to the Puzzle." *Nature. Med.* 2(10) 1077–8.

Starka, L., Hampl, R., Bicikova, M. and Obenberger, J. 1976. "Identification and Radioimmunologic Estimation of Sexual Steroid–Hormones in Aqueous Humor and Vitreous of Rabbit Eye." *Albrecht v. Graefes Arch. Klin. Exp. Ophthal.* 199:261–266.

Tripathi, R.C. and Tripathi, B.J. 1983. "Lens Morphology, Ageing and Cataract." *Journal of Gerontology*, 38:258–270.

Worgul, B.V. 1982. "Lens". *Ocular Anatomy, Embryology and Teratology.* F. A. Jakobiec, editor. Harper and Row, Philadelphia. 355–389.

Klein, B.E.K., "Lens Opacities In Women In Beaver Dam, Wisconsin: Is There Evidence Of An Effect Of Sex Hormones?" From The Department of Ophthalmology, University of Wisconsin Medical School, Madison, pp 517–544.

Majima K. "Cell biological analysis of the human cataractous lens: implication of lens epithelial cells in the development of aftercataract." *Ophthalmic Research.* 27(4):202–7, 1995.

METHOD FOR PREVENTING OR CONTROLLING CATARACT

TECHNICAL FIELD

The present invention relates to a method for preventing or controlling pathological changes which occur in association with cataract formation in the mammalian eye by protecting lens cells against the cataractogenic effects of transforming growth factor-β (TGFβ). In particular, the present invention relates to a method for preventing or controlling TGFβ-induced cataract formation in the mammalian eye by administering an estrogen or estrogenic substance to the mammal.

BACKGROUND ART

Cataract is an opacity of the lens that interferes with vision. It is one of the most common of eye diseases and, though it may occur at any time in life, it often accompanies aging. In the USA, for example, up to 45% of people aged between 74 and 89 years suffer from cataract. Predisposing factors include aging, diabetes, UV/sunlight, ocular surgery and malnutrition. Cataracts are most frequently classified according to the location of the lens opacity: nuclear, cortical, posterior subcapsular or anterior subcapsular (Tripathi and Tripathi, 1983). Currently, the most commonly used treatment for cataract is surgical removal of the lens cells and subsequent implantation of a synthetic replacement lens within the remaining lens capsule. However, implantation of a synthetic lens may only temporarily restore vision because residual cells associated with the lens capsule often grow to form new opacities. The latter condition is a form of cataract known as aftercataract and also known as posterior capsule opacification (Green and McDonnell, 1985; Kappelhof and Vrensen, 1992).

The inventors have previously shown that TGFβ is cataractogenic. The inventors have also shown that the TGFβ-induced changes to lens cells can be inhibited or prevented by reducing or inhibiting the action of TGFβ, such as by administering an effective amount of one or more inhibitors of TGFβ. This was disclosed in PCT/AU94/00694, the entire specification of which is incorporated into this patent specification by reference.

The inventors' previous work has shown that TGFβ induces certain changes known to be associated with cataract, including anterior and posterior subcapsular cataract and aftercataract. These changes have been shown in rat lens explants cultured with TGFβ and include accumulation of extracellular matrix, formation of spindle-shaped cells, capsule wrinkling and cell death with features of apoptosis (Liu et al., 1994; Hales et al., 1994). Further evidence of TGFβ involvement in anterior subcapsular cataract formation comes from whole rat lens studies which show that TGFβ induces anterior opacities that coincide with subcapsular plaques containing molecular markers for cataract, α-smooth muscle actin and collagen type I (Hales et al., 1995). These proteins are not normally found in the lens but are present in certain forms of cataract in humans. The other changes discussed above are known to be associated with certain forms of cataract in humans. Further evidence of TGFβ involvement in posterior subcapsular cataract and cortical cataract formation comes from studies described in Examples 1 and 3.

Sex-dependent and female sex hormone-related differences in susceptibility to cataract formation have been noted in epidemiological studies. While the prevalence and severity of cataract increases with aging in both men and women, a more marked increase occurs in women than in men later in life, over the time period when serum levels of sex hormones are low in women (Klein et al., 1992). Furthermore, early age at menarche or delayed menopause seems to protect against certain forms of cataract (Klein, 1993). Such studies do not provide evidence that the sex-(or sex hormone-) related protective effect observed is due to estrogen. In addition, researchers have reported the prevalence and severity of nuclear, cortical and posterior subcapsular cataracts in postmenopausal women on hormone replacement therapy, involving administration of pharmaceutical products containing 'estrogen' with or without 'progesterone', and in others not undergoing hormone replacement therapy (Klein, 1993). A statistically significant difference between these two groups of women was found for nuclear cataract only, and it is not clear whether the observed effect of hormone replacement therapy was due to estrogen. To date there is no evidence that estrogen per se has a protective effect against forms of cataract induced by TGFβ or that a TGFβ-linked process is involved in protecting individuals against cataract in such studies.

Some animal studies, however, teach that estrogen causes cataract or cataract-like changes in the lens. Progesterones and estrogens in vitro have been noted to lead to an increase in ion permeability which is accompanied by loss of clarity in cultured lenses (Lambert, 1968). It has also been reported that intramuscular injection of estrogen causes changes in the lens epithelium resulting in atrophy which may be a factor in the development of lenticular opacity (Bisaria, 1980).

Starka et al. (1976) have reported detecting estrogens in the ocular media in female and male rabbits but it is not clear what levels of active hormone are present.

According to published scientific literature, the effect of estrogen on the biological activity of TGFβ is variable. Estrogens have been known to enhance the biological activity of TGFβ. For example, 17-β-estradiol has been reported to stimulate release of active TGFβ when added to cultures of rat granulosa cells (Dorrington et al., 1993). In addition, Herman et al. (1994) report an enhancing effect of estrogen on TGFβ activity by showing that removing estrogen from the medium of cultured human breast cancer cells reduces their sensitivity to the growth-inhibitory effects of TGFβ. Estrogens are also known to have a suppressive effect on TGFβ activity or no effect. For example, estrogen-induced tumorigenesis in the anterior pituitary of rats is accompanied by a loss of sensitivity to TGFβ1 (Pastorcic et al., 1995), and estradiol does not specifically block the growth-inhibitory effects of TGFβ in hepatocyte cultures, although the cells are otherwise responsive to estradiol (Ni and Yager, 1994). Similarly, in studies on the expression of TGFβ mRNA and protein rather than TGFβ biological activity, no consistent trend is apparent i.e. estrogen may upregulate, downregulate or have no effect on TGFβ expression depending on both the cell type and the TGFβ isoform involved.

Many postmenopausal women are now receiving estrogen replacement therapy, in conjunction with progesterone where appropriate, but it is not universally advocated or available. In 1994, it was reported that only 5 to 10% of menopausal women in the USA were receiving this treatment (Griffing and Allen, 1994).

The TGFβ family consists of a group of related proteins; TGFβ1, TGFβ2 and TGFβ3 are the isoforms found in mammals. Mature TGFβ in its biologically active form is a 25 kDa dimer that is cleaved from a latent precursor molecule (Kingsley et al., 1994).

DISCLOSURE OF THE INVENTION

In one aspect, the present invention provides a method of preventing or controlling TGFβ-induced cataract or cataract-like disorders in the eye of a mammalian subject which comprises administering to the subject an effective amount of estrogen.

In another aspect, the present invention provides a method of preventing or controlling TGFβ-induced cataract or cataract-like disorders in the eye of a mammalian subject which comprises administering directly to or near to the eye of the subject an effective amount of estrogen.

Preferably, the mammalian subject is a human being but the present invention is also suitable for treating TGFβ-induced cataract or cataract-like disorders in other animals such as horses, cats, dogs or the like.

Even though the present invention is suitable for prevention or treatment of cataract in humans irrespective of their natural estrogen levels, the present invention is particularly suitable for treating women with low estrogen levels, ie. peri- and post-menopausal women or women suffering hypoestrogenism for other reasons, for example, hypogonadism, ovariectomy or primary ovarian failure.

In a further aspect, the present invention provides an ophthalmological formulation comprising estrogen in an ophthalmologically acceptable carrier.

In a further aspect, the present invention provides a membranous ocular patch impregnated with estrogen.

In a further aspect, the present invention provides a method of preventing or controlling aftercataract formation in the eye of a mammalian subject following lens implant surgery which comprises implanting in the eye of the subject, a lens or lens implant coated or impregnated with estrogen.

In yet another aspect, the present invention provides a lens implant coated or impregnated with estrogen.

In yet a further aspect, the present invention provides the use of estrogen in the manufacture of an ophthalmological formulation for preventing or controlling TGFβ-induced cataract or cataract-like disorders.

Estrogens are mammalian sex hormones that occur in both males and females throughout life. While their major role is in the reproductive biology of the female, they also influence various tissues that are not part of the reproductive system. In humans, the naturally occurring estrogens are estradiol (17-β-estradiol), estrone and estrone sulphate, with smaller amounts of conjugated or hydroxylated derivatives; estradiol is the most active of these biologically (Lobo, 1987).

Many substances, both naturally occurring and synthetic, are classed as estrogens on the basis of their therapeutic or biological action (see listing under 'Estrogens' in the 'Therapeutic Category and Biological Activity Index' of The Merck Index, 12th Edition, Merck Research Laboratories, NJ, 1996, page THER-22). According to this listing, estrogens may be steroids (e.g. estradiol, ethinyl estradiol, colpormon, conjugated estrogenic hormones, equilenin, equilin, estriol, estrone, mestranol, moxestrol, mytatrienediol, quinestradiol and quinestrol) or non-steroids (e.g. diethylstilbestrol, dienestrol, benzestrol, broparoestrol, chlorotrianisene, dimestrol, fosfestrol, hexestrol, methallenestril, methestrol). The substances listed do not necessarily exert their biological effect(s) directly; some require metabolic conversion to an active form after administration. For example, estrone sulphate administered orally is metabolised by various pathways, leading to increased serum levels of the more active estradiol, while mestranol is converted to the highly potent ethinyl estradiol after administration. Other non-steroidal estrogens include indenestrol.

Many additional substances are known to be estrogenic, that is, they interact with cellular estrogen receptors and mimic the effects of estrogens. Many classes of such estrogenic substances have been shown to be tissue selective in their estrogenic effects. Diverse classes of molecules fall within this category, for example: quinolines and fused quinolines that act as steroid receptor modulators such as 3,9-dihydroxy-5H-benzofuro[3,2-c]quinoline-6-one and those disclosed in WO 96/19458; phytoestrogens which occur naturally in plants such as forage plants, soya beans, seeds, berries and nuts (Jordan et al., 1985), including isoflavones such as genistein and genistein glycosides, equol, O-desmethyl-angolensin, biochanin A, daidzein and formononetin; flavones such as phloretin, 4'-6-dihydroxyflavone and tricin, and coumestans such as coumestrol, 4'-Omethyl coumestrol, medicagol and sativol, lignans such as matairesinol, enterodiol, enterolactone, guaiaretic acid, nordihydroguaiaretic acid and derivatives thereof, β-sitosterol; mycoestrogens such as zeranol, zearalenol and zearalenone; estrogen receptor agonist/antagonists, such as tamoxifen, hydroxytamoxifen, zindoxifene and its metabolites, nafoxidene and derivatives, clomiphene, centchroman, benzothiophenes and related compounds such as benzothiophene-derived LY139478 (Eli Lilly), raloxifene and droloxifene, which may mimic the action of estrogens in certain types of cells, while opposing it in others (Raisz, 1996); and many phenols that contain a strategically located phenolic hydroxyl not impaired by an alkyl substitution in the ortho position (see Jordan et al., 1985), including octyl phenyl, nonyl phenol, butylated hydroxyanisole, bisphenol A and trihydroxy-8-prenylflavone. Note that estrogenic substances in this general category may also be referred to in the literature as 'estrogens' (see Jordan et al., 1985, for example). As already described above (for 'estrogens' as defined in Merck), estrogenic substances may exert their estrogenic effect(s) directly or they may require metabolic conversion to an active form after administration. For example, metabolic activation of some phytoestrogens involves demethylation to phenols (Jordan et al., 1985).

Furthermore, a substance may exert an estrogenic effect in the following ways. It may enhance the effect of endogenous estrogens, that is, estrogens already present in a recipient (e.g. by increasing the number of estrogen receptors), or it may enhance the biological effect(s) of endogenous estrogens by promoting conversion to a more potent form or by inhibiting their degradation.

As used throughout this specification including the claims, the term estrogen is intended to include all forms of estrogens and estrogenic substances as discussed above, including estrogen receptor agonist/antagonists whose action on the lens mimics the effects of estrogens. Derivatives, precursors, metabolites and the like of all of the substances discussed above whose action on the lens mimics the effects of estrogens are also encompassed by the term "estrogen". Specifically, naturally occurring estrogens, synthetic estrogens, steroidal and non-steroidal estrogens and estrogenic substances are all typically suitable for use in the present invention. A combination of two or more estrogens is also suitable for use in the present invention. Accordingly, as used throughout this specification including the claims, the term estrogen also includes a combination of two or more estrogens.

BRIEF DESCRIPTION OF THE DRAWINGS

FIG. 1 shows micrographs of lenses from male and female Wistar rats. Lenses were cultured with 0.15 ng/ml TGFβ2 and photographed after 7 days.

FIG. 2 shows micrographs of lenses from ovariectomised rats. Lenses were cultured with 0.15 ng/ml TGFβ2 and photographed after 7 days.

BEST AND OTHER MODES FOR CARRYING OUT THE INVENTION

Figure 1A:
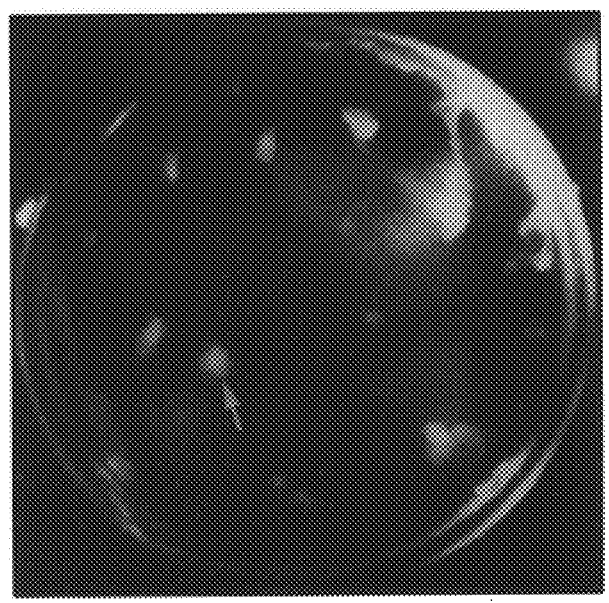
FIG. 1A shows a typical lens from a male rat, which developed distinct anterior opacities (arrow).

Commercially available estrogens or estrogenic substances which may be used in accordance with the present invention include estradiol, ethinyl estradiol, equilin, estriol, estrone, 6-hydroxyquinoline, coumestrol, formononetin, equol, daidzein, zearalenol, nafoxidene, octyl phenol, mestranol, quinestrol, diethylstilbestrol, genistein, biochanin A, phloretin and tamoxifen. Other estrogens and estrogenic substances can be easily prepared according to literature procedures.

Estrogen can be administered according to the present invention by introduction into one or more chambers of the eye (for example, the anterior chamber) or near the eye, by an injection into a site from which the estrogen can be readily transported to the eye via the circulatory system, or by oral administration or injection to the subject, or by topical application such as in a cream or nosespray.

Estrogen may also be administered in the form of dermal patches or by implantation of a depot of estrogen for slow release. The estrogen may also be administered through a membranous ocular patch which is applied directly to the surface of the eye. Routes of administration of estrogens as discussed by Lobo (1987) are suitable for the present invention.

The effective amount of estrogen required for use in the treatment according to the present invention will vary with the estrogen used, with the route of administration, the stage of condition under treatment and the host undergoing treatment, and it is ultimately at the discretion of the physician. A dosage that results in the exposure of the lens cells to a concentration of the estrogen bioequivalent to about $10^{-9}$ to $10^{-11}$ molar 17-β-estradiol is suitable.

Typically the estrogen is presented as a pharmaceutical or ophthalmological formulation.

The treatment with estrogen can be used as an adjunct to eye surgery to inhibit cataract-related changes that may occur as a result of surgical intervention as, for example, in the formation of aftercataract following surgery for treatment of some other form of cataract. The present invention may also be suitable for treatment of individuals otherwise at a greater than normal risk of cataract formation or of being exposed to elevated TGFβ levels near the lens.

Pharmaceutical and ophthalmological formulations of the present invention are prepared according to conventional pharmaceutical formulating techniques. The carrier may be of any form depending on the form of the preparation desired for administration and the formulation may optionally contain other therapeutic ingredients. Typically estrogen can be included in conventional irrigation solutions or viscoelastic solutions used during ocular surgery (Black, 1996). Lens implants coated or impregnated with estrogen may contain other therapeutic agents and may be prepared according to conventional techniques.

EXAMPLE 1

Effect of estrogen in vivo on TGFβ-induced cataract.

METHOD

17-β-estradiol (1,3,5[10]-Estratriene-3, 17β-diol) and progesterone (4-Pregnene-3, 20-dione) were obtained from Sigma (St Louis, Mo.) and human recombinant TGFβ2 from Genzyme (Cambridge, Mass.). In some experiments, lenses were derived from normal 6- to 10-month-old adult male and female Wistar rats, sacrificed by $CO_2$ asphyxiation before removal of eyes. Alternatively, ovariectomies were performed on 3-month-old female Wistar rats under anaesthesia as described by Murphy and Rogers (1981). After waiting for 4 to 5 weeks to ensure clearance of residual estrogen and progesterone, ovariectomised rats were given three daily injections of 0.5 µg 17-β-estradiol or 5 mg progesterone, dissolved in benzyl alcohol/peanut oil (1:3, v/v). Control rats received vehicle alone. One day later, rats were sacrificed by a lethal dose of nembutal (Boehringer, NSW, Australia) before removal of eyes.

Lens Cultures

Lenses were carefully dissected free from surrounding ocular tissues in culture medium, as described by Hales et al. (1995), and cultured with TGFβ2 at final concentrations of 0.025–4 ng/ml, which was added immediately. Recombinant human TGFβ2 was obtained from Genzyme (Cambridge, Mass., USA). Serum-free medium 199 containing antibiotics and 0.1% bovine serum albumin, as already described by Hales et al. (1995), was used as culture medium. Controls received no TGFβ. Culture medium was renewed every two days throughout the culture period, without further addition of TGFβ. Lenses were cultured for 7 days and the anterior surface was photographed daily to record development of opacities. At the end of the culture period, lenses were fixed in Carnoy's fixative (acetic acid/ethanol, 1:3, v/v) and embedded in paraffin.

Opacification Index

TGFβ-induced lens opacification begins as diffuse clouding on the anterior surface of the lens. As the response progresses, these regions condense to form distinct opacities leaving a reduced area of clouding. At low concentrations of TGFβ, few distinct opacities are observed at 7 days culture and a large proportion of the lens surface remains cloudy. In contrast, at high concentrations most of the initially cloudy areas condense to form numerous distinct opacities (as in FIG. 1A). On the basis of these observations, a method for measuring the extent of opacification has been developed.

Micrographs of lenses at 7 days of culture were used to determine lens opacification. Each micrograph was scanned with a 3CX X-ray scanner (XRS Corporation, CA, USA) using Adobe Photoshop and XRS Omni Media software. A series of measurements was then made using NIH Image v 1.52. In some micrographs, flared reflections of the light source made it impossible to assess the extent of opacification in certain regions (see, for example, FIG. 1B). Only micrographs in which the accessible area represented greater than 75% of the total area were used. The accessible area (A) and, within this area, the total area of clouding (B) and the total number of distinct opacities (C) were measured. An 'opacification index' was then calculated as follows:

$$\text{Opacification Index} = \frac{\text{number of distinct opacities } (C)}{\text{proportion of assessable area with clouding } (B/A)}$$

Histology and Immunohistochemistry

Serial sections of paraffin-embedded lenses, were processed for routine histology or for immunohistochemical localisation of α-smooth muscle actin or type I collagen, as described by Hales et al. (1995). Representative lenses from each treatment group were examined by routine histology (all TGFβ2 concentrations) and immunolocalisation (0.15 ng/ml TGFβ2).

RESULTS

Male-female Difference in Responsiveness of Lenses to TGFβ

Figure 1B:
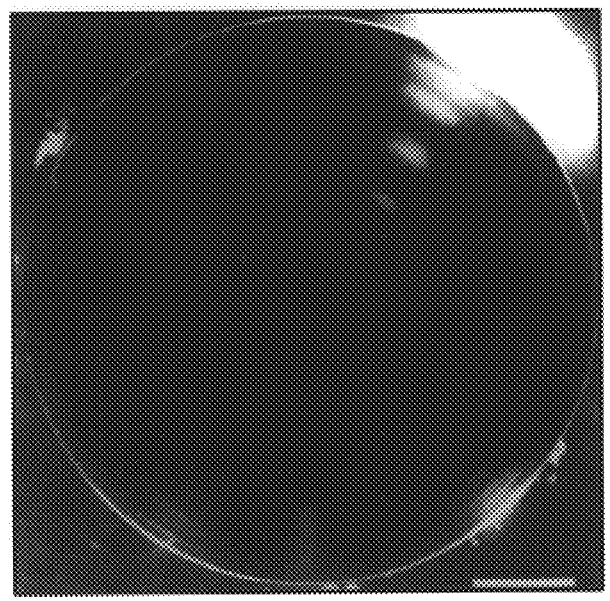
FIG. 1B shows a typical lens from a female rat. Some flaring of the light source is evident in the upper right-hand quadrant of each lens. Scale bar 400 μm.

Lenses from male rats developed distinct anterior opacities when cultured with 0.15 ng/ml TGFβ2 (FIG. 1A). In contrast, lenses from female rats remained transparent under these conditions (FIG. 1B), as did control lenses from male and female rats cultured without TGFβ (not shown). However, at a higher concentration of TGFβ2, 1 ng/ml, lenses from female rats also developed opacities (Table 1). For both sexes, the response increased significantly with concentration of TGFβ.

TABLE 1

TGFβ-induced opacification in lenses from adult rats

| | Opacification Index | |
|---|---|---|
| TGFβ (ng/ml) | Male | Female |
| 0 | 0 | 0 |
| 0.025 | 13 ± 0.3 | 0* |
| 0.15 | 57 ± 5 | 0* |
| 1 | 69 ± 9 | 54 ± 6 |
| 4 | 187 ± 19 | 118 ± 10* |

Lenses from adult male and female rats were cultured for 7 days. TGFβ2 was used at the concentrations indicated. Values represent the mean ± SEM of determinations of four individual lenses. *This value is significantly lower than the corresponding value for lenses from male rats (p < 0.05 Students t test).

Histological examination of lenses cultured with 0.15 ng/ml TGFβ2 revealed distinct subcapsular plaques, containing spindle-shaped cells and extracellular matrix, in the lenses from males. In contrast, the lenses from females and controls retained normal lens architecture, with a monolayer of epithelial cells overlying the fibre mass. Immunolocalisation of α-smooth muscle actin and type I collagen showed that, for males, strong reactivity for both these cataract markers was present in plaques induced by culturing with 0.15 ng/ml TGFβ2, whereas corresponding lenses from females showed no reactivity for α-smooth muscle actin and only very weak reactivity for type I collagen in a few cells in the epithelium. These markers were not detectable in sections of control lenses from males or females cultured for up to 7 days without TGFβ.

Figure 2A:
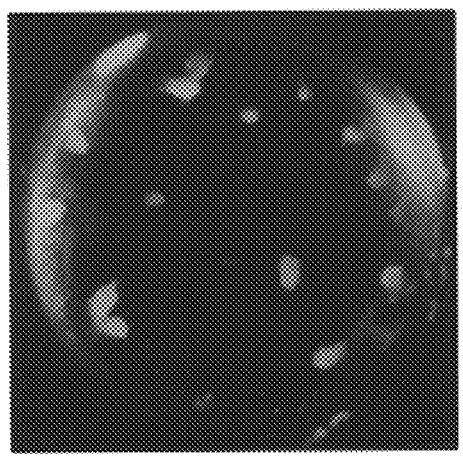
FIG. 2A shows a lens from a rat that received vehicle only.
Figure 2B:
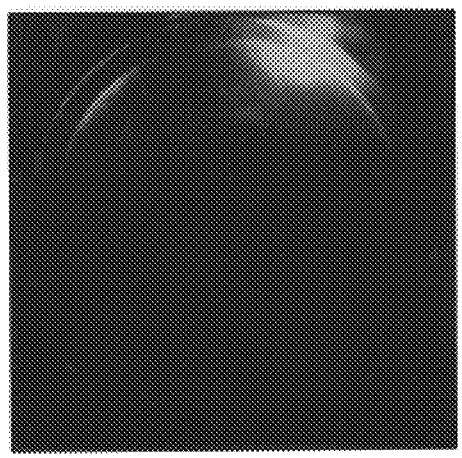
FIG. 2B shows a lens from a rat that received estrogen replacement.
Figure 2C:
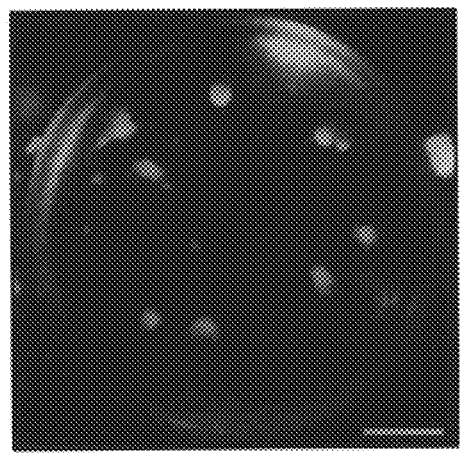
FIG. 2C shows a lens from a rat that received progesterone replacement. Scale bar 400 μm.

Effect of Hormone Replacement, Following Ovariectomy, on Lens Responsiveness to TGFβ in vitro Lenses from ovariectomised rats (without hormone replacement) developed opacities when cultured with 0.15 ng/ml TGFβ (Table 2; FIG. 2A), a concentration shown to have negligible effect on lenses from normal female rats (Table 1, FIG. 1B). Lenses from ovariectomised rats which received estrogen, however, did not develop opacities under these conditions (Table 2; FIG. 2B), while the response of lenses from rats treated with progesterone was similar to that of lenses from vehicle-treated rats (Table 2; FIG. 2C).

TABLE 2

TGFβ-induced opacification in lenses from ovariectomised rats on various hormone replacement regimes

| Hormone regime | Opacification index |
| --- | --- |
| Vehicle only | 240 ± 18 |
| 17-β-estradiol | 0 |
| Progesterone | 210 ± 19* |

TGFβ2 (0.15 ng/ml) was used and lenses were cultured for 7 days. Values represent the, mean ± SEM of determinations of six individual lenses.
*This value is not significantly different from the value for controls (vehicle alone).

Figure 3A:
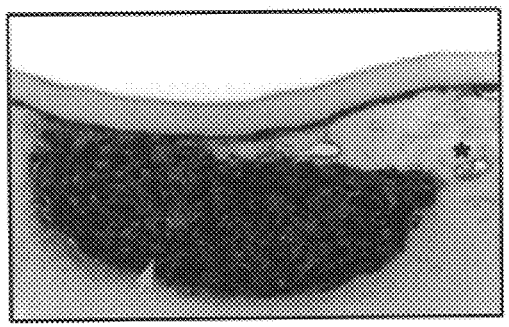
FIG. 3 shows micrographs of lenses from ovariectomised rats that received vehicle alone (FIGS. 3A, 3C and 3E) or estrogen replacement (FIGS. 3B, 3D and 3F). Lenses were cultured with 0.15 ng/ml TGFβ2 and fixed at the end of a 7 day culture period. Serial sections were stained with haematoxylin and eosin (FIGS. 3A and 3B) or used for localisation of α-smooth muscle actin (FIGS. 3C and 3D) and type I collagen (FIGS. 3E and 3F). The arrow in FIG. 3A indicates spindle-shaped cells within a large anterior subcapsular plaque containing many condensed nuclei; the asterisk indicates swollen fibre cells around the plaque where vacuoles are also present. The arrowheads in FIG. 3C and FIG. 3E indicate the cells attached to the capsule that contain α-smooth muscle actin and type I collagen, respectively. ep, epithelial cells; ca, lens capsule; fc, fibre cells. Scale bar 40 μm.
Figure 3B:
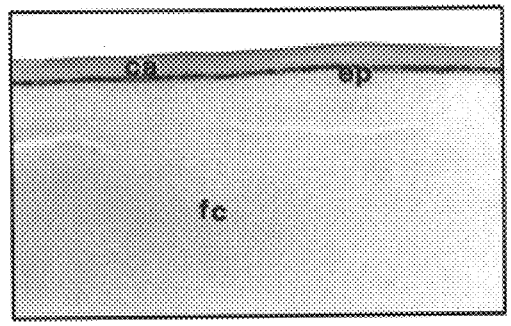
Figure 3C:
Figure 3D:
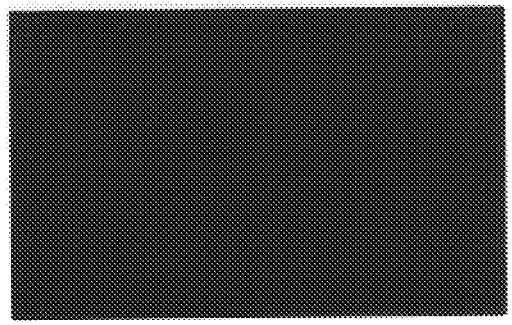
Figure 3E:
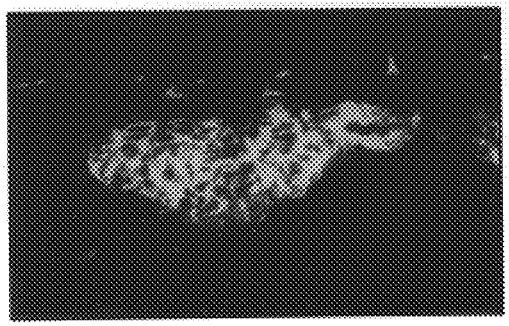
Figure 3F:
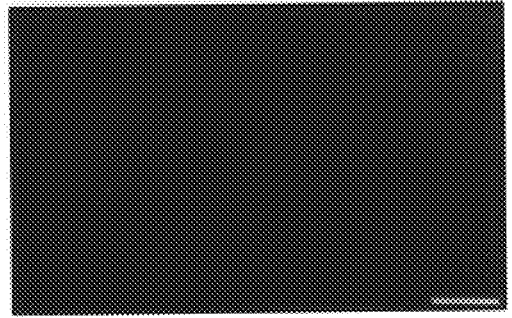

Histologically, the opacities observed in ovariectomised rats that only received vehicle corresponded with subcapsular plaques or clumps of abnormal cells (FIG. 3A). Reactivity for the cataract markers α-smooth muscle actin and type I collagen was observed predominantly within the subcapsular plaques (FIGS. 3C and 3E). In contrast, lenses from estrogen-treated rats retained normal cellular morphology (FIG. 3B) and no reactivity for α-smooth muscle actin or type I collagen was detected (FIGS. 3D and F). In all these respects, lenses from rats that received progesterone replacement were indistinguishable from lenses from rats that received vehicle alone.

Figure 4A:
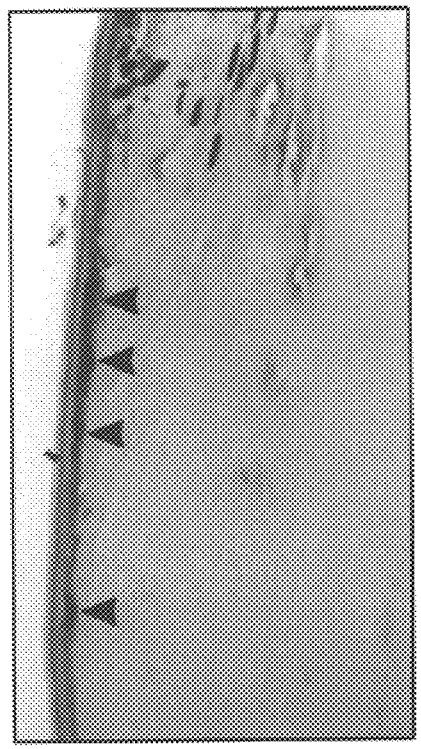
In FIGS. 4A and 4C, the arrowheads indicate nucleated cells migrating along the lens capsule towards the posterior pole. Scale bar 40 μm.
Figure 4B:
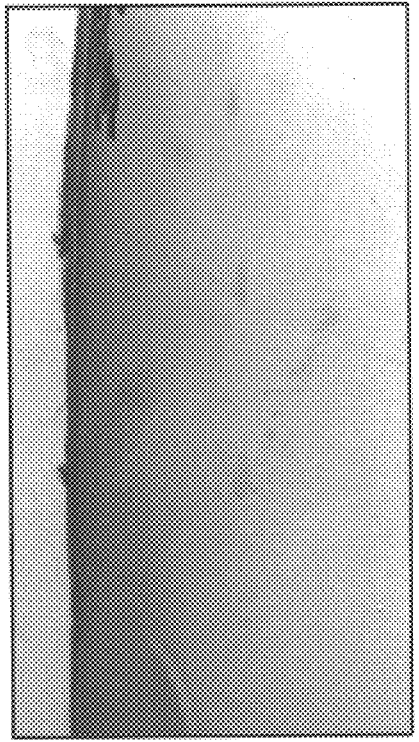
FIG. 4 shows lenses from ovariectomised rats that received vehicle alone (FIGS. 4A and 4C) or estrogen replacement (FIGS. 4B and 4D). Lenses were cultured with 0.15 ng/ml TGFβ2 and fixed at the end of the 7 day culture period. Serial sections were stained for routine histology with haematoxylin and eosin (FIGS. 4A and 4B) or used for immunofluorescent localisation of type I collagen (FIGS. 4C and 4D). The lens equator is positioned at the top of each micrograph.
Figure 4C:
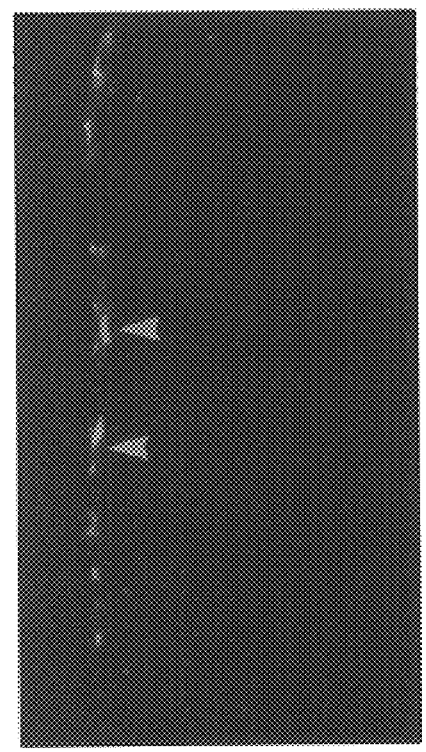
Figure 4D:
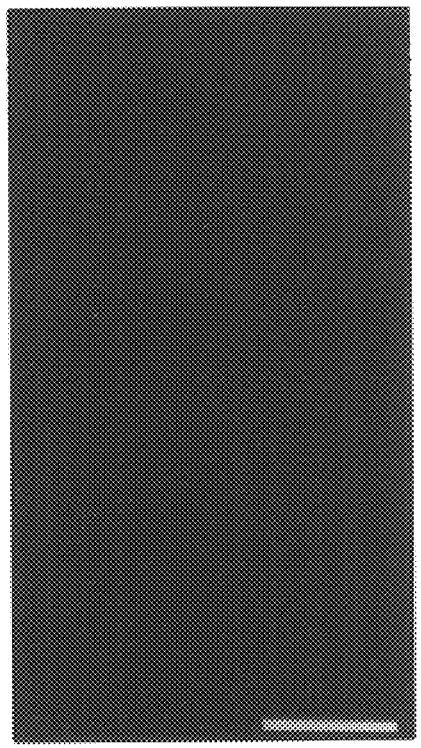

A variety of more subtle histological changes were observed in lenses from ovariectomised rats that did not receive estrogen. Swelling of cortical fibre cells with evidence of degeneration, reminiscent of cortical cataract, was commonly observed (see, for example, FIG. 3A), generally in the region of the lens anterior to the equator. In addition, nucleated cells were observed migrating along the posterior capsule towards the posterior pole (see, for example, FIG. 4A); these cells showed reactivity for type I collagen (FIG. 4C) but not for α-smooth muscle actin. None of these changes was observed in lenses from estrogen-treated ovariectomised rats, which remained transparent (FIGS. 4B and D). In lenses from normal male and female rats, concentrations of TGFβ higher than 0.15 ng/ml were required to induce changes as pronounced as those in FIGS. 3A and 4A. Thus lenses from normal rats of either sex seemed to be more resistant to the effects of TGFβ than those from ovariectomised rats that did not receive estrogen.

It has previously been shown that all mammalian isoforms of TGFβ induce cataractous changes in lens explants and cultured lenses, TGFβ2 and TGFβ3 being more potent than TGFβ1 (de Iongh et al., 1997). The present study shows that the ovarian estrogen, 17-β-estradiol, protects rat lenses against TGFβ-induced cataract and that susceptibility to the cataractous changes induced by TGFβ is sex-dependent. Culturing lenses from ovariectomised females with TGFβ resulted in marked opacification of the lens. Estrogen replacement in vivo prevented this response, but progesterone replacement did not (Table 2; FIG. 2). Furthermore, lenses from male rats were found to be more susceptible to the cataractogenic effects of TGFβ than those from normal females (Table 1; FIG. 1) and lenses from normal rats of either sex seemed more resistant to the effects of TGFβ than those from ovariectomised rats (cf. Tables 1 and 2). The latter results are also consistent with a protective role for estrogen, since circulating estrogen is present in male rats, albeit at much lower levels than in normal females.

Opacities induced by TGFβ correspond with subcapsular plaques of aberrant cells, including spindle-shaped cells, which are often associated with wrinkling of the lens capsule. Abnormal extracellular matrix deposition also occurs, mainly in the plaques. All these changes are typical of anterior and posterior subcapsular cataract and aftercataract. In addition, TGFβ induces the accumulation of α-smooth muscle actin and type I collagen in both explants and cultured lenses (Hales et al., 1994; Hales et al., 1995). These proteins, which are not generally found in the lens, are present in human anterior subcapsular cataract and in aftercataract.

The present study shows that in lenses from adult rats, as for weanlings, TGFβ induces opacities with morphological and molecular features of cataract. In each case, the plaques associated with the opacities are morphologically indistinguishable from early stage human anterior subcapsular cataracts (Worgul, 1982).

The opacities that form in rat lenses cultured with TGFβ are anterior subcapsular cataracts. Marked similarities between TGFβ-induced cataract and aftercataract have already been noted (Liu et al., 1994; Hales et al., 1995). Evidence of subtle changes typical of posterior subcapsular cataract and cortical cataract is provided by the present study. The present study provides evidence that TGFβ can induce migration of aberrant cells along the lens capsule towards the, posterior pole (as in FIG. 4A). A similar abnormal migration of nucleated cells along the posterior capsule, is thought to be the basis of human posterior subcapsular cataract formation (Eshagian, 1982). Some evidence of TGFβ-induced cataract-like change was also observed in the cortical fibres in the present study (FIG. 3A). This study of rats of varying natural or induced estrogen status provides evidence that estrogen protects against TGFβ-induced cataract.

EXAMPLE 2

Ovariectomised rat model: effect on TGFβ-induced cataract of administering 17-β-estradiol directly to the lens.

Method

Lenses from ovariectomised rats were precultured for two days with or without $10^{-10}$ M 17-β-estradiol; phenol red-free minimal essential medium (Sigma), containing 0.1% bovine serum albumin and antibiotics, was used. The medium was then replaced and TGFβ (0.15 ng/ml) was added immediately. After a further seven days culture, the opacification index was determined in the same manner as described above for Example 1.

Results

The estrogen-treated lenses showed negligible opacification in response to TGFβ. While a small region of haziness was observed at the centre of some of these lenses within six days of adding TGFβ, no tendency to condense into discrete opacities with time was noted. Numerous distinct opacities developed in corresponding lenses cultured in parallel without the addition of estrogen as shown in Table 3.

TABLE 3

Effect of estrogen exposure in vitro on TGFβ-induced opacification of lenses from ovariectomised rats

| Treatment | Opacification index |
|---|---|
| 17-β-estradiol | 0 |
| No estradiol | 151 ± 19 |

Lenses from ovariectomised rats were precultured for 2 days with or without $10^{-10}$ M 17-β-estradiol, as indicated. Medium was then replaced (with or without estradiol, as before) and TGFβ2 (0.15 ng/ml) was added immediately. After a further 7 days culture, the opacification index was determined. Values represent the mean ± SEM of determinations of three individual lenses.

This study involving administration of estrogen to lenses in vitro provides evidence that estrogen protects against TGFβ-induced cataract by influencing lens cells directly. Thus it also seems likely that estrogen confers protection against cataract by targeting lens cells directly when administered in vivo (as in Example 1), although the possibility of additional indirect benefits is not excluded.

EXAMPLE 3
Induction of cataract by administering TGFβ in vivo.

Method

Three 9-month-old male Wistar rats (ex-breeding colony) were used in this study. Each rat was anaesthetised using 5% halothane in 70% $NO_2$/30% $O_2$. The concentration of halothane was then reduced to 1.5% for the duration of all surgical procedures. The rat was then positioned under a dissecting microscope with its left eye uppermost. Using a fine needle (Beckton Dickinson, USA; external diameter 360 μm), a small puncture was made in the region of the limbus. A very fine needle (Hamilton, USA; external diameter 200 μm) attached to a 10 μl syringe (Hamilton) was immediately lowered through the puncture hole into the vitreous using a modified micromanipulator (Narashige, Japan). 3 μl of TGFβ2 (using 20 ng/μl solution supplied by Genzyme) was then slowly injected into the vitreous. The needle was left in position for 30 to 60 seconds then slowly withdrawn to minimise fluid loss from the eye. Each injection procedure was performed under a dissecting microscope to ensure correct positioning of the needle and to monitor any loss of fluid from the eye. After injection, each animal was placed in a warmed recovery box. Once all rats had been injected with TGFβ, each rat was anaesthetised for a second time, and the same protocol used to inject the right eye with 3 μl vehicle alone (30% acetonitrile/0.1% trifluoroacetic acid) to serve as a control.

Rats were sacrificed by $CO_2$ asphyxiation 6, 12 or 15 weeks after injection and the eyes were removed and placed in culture dishes containing medium 199. Lenses were carefully dissected free from surrounding ocular tissues and examined for the presence of opacities, photographed, fixed and processed for routine histology and immunolocalisation (as described in Example 1).

Results

All lenses from TGFβ-injected eyes showed evidence of opacification and changes in cytoarchitecture, whereas control lenses remained transparent and retained normal morphology. None of the lenses in this study, that is control or TGFβ-treated, displayed evidence of penetration of the needle into the lens capsule during the injection procedure.

After exposure to TGFβ in vivo, lenses tended to develop opacities associated with subcapsular plaques of abnormal cells, similar to those observed in lenses cultured with TGFβ (see Example 1). However, these appeared to be restricted to a region around the lens equator extending some distance towards the anterior and posterior poles of the lens. More diffuse clouding was observed throughout most of the lens.

Figure 5A:
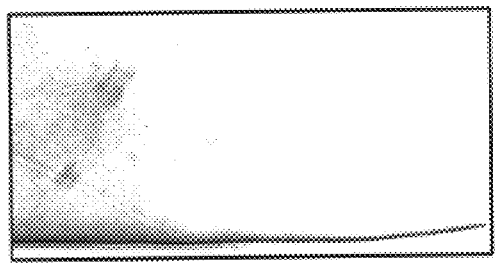
FIG. 5 shows micrographs of lenses from rats that had received intravitreal injections of vehicle only (FIGS. 5A and 5C) or TGFβ2 (FIGS. 5B and 5D). Serial sections were stained for routine histology with haematoxylin and eosin (FIGS. 5A and 5B) or left unstained and viewed by phase contrast microscopy (FIGS. 5C and 5D). The arrowheads in FIGS. 5B and 5D indicate nucleated cells, most of which show varying degrees of swelling. ca, posterior lens capsule. Scale bar 40 μm (FIGS. 5A and 5B); 25 μm (FIGS. 5C and 5D).
Figure 5B:
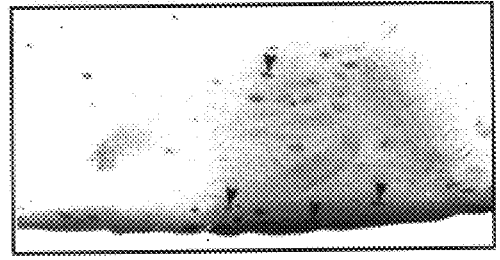
Figure 5C:
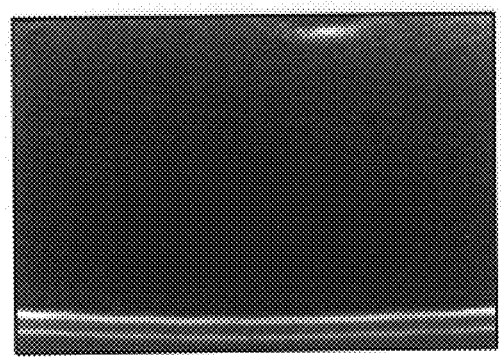
Figure 5D:
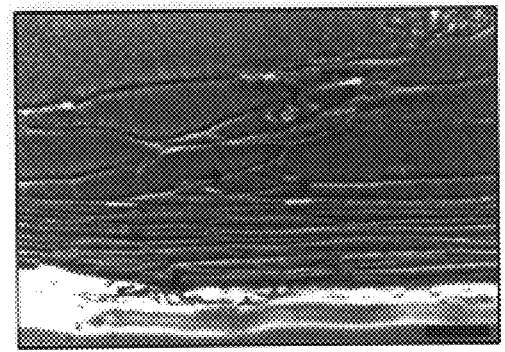
Figure 6A:
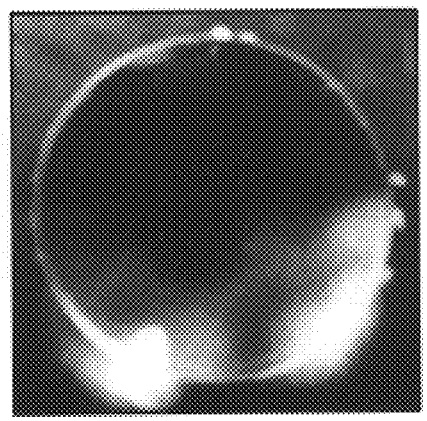
FIG. 6 shows examples of lenses corresponding to categories used for grading TGFβ-induced cataractous changes in lenses from immature female rats. Grade 1: lens exhibits slight clouding on visual examination that is not apparent in micrograph (A); Grade 2: lens exhibits extensive graininess (B) or a single central opacity (C). Grade 3: lens contains two to three discrete opacities (D). Grade 4: lens contains more than three discrete opacities. Some flaring of the light source is evident especially in the lower portion of each lens. Scale bar, 420 μm.
Figure 6B:
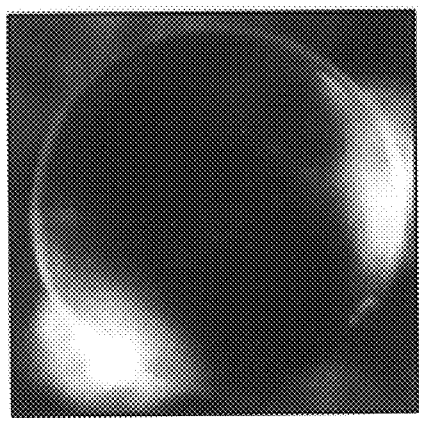
Figure 6C:
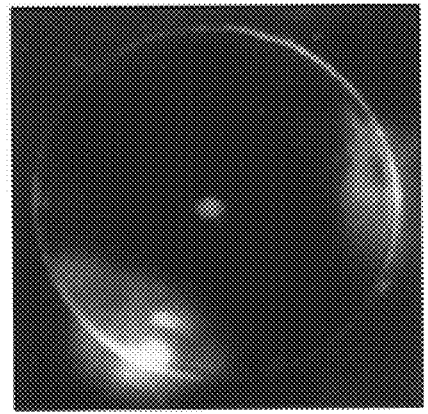
Figure 6D:
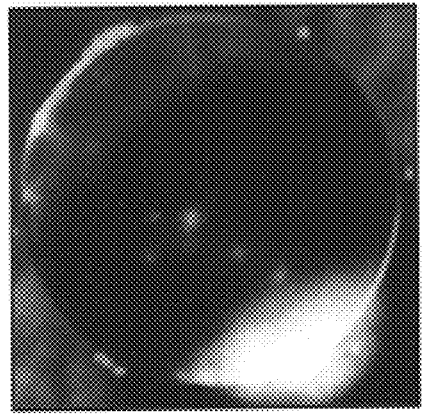
Figure 6E:
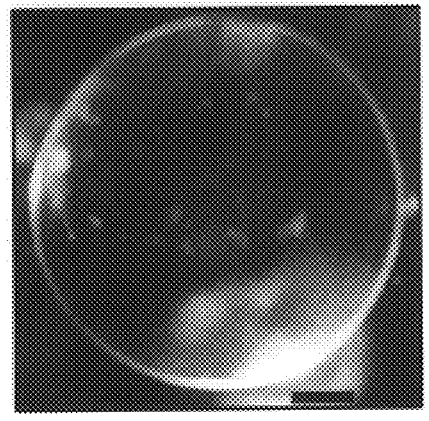

Normal lens morphology was observed in controls. For example, in the posterior region, fibre cells were regularly aligned parallel to the lens capsule and no nuclei were present (FIGS. 5A and 5C). In lenses that had been exposed to TGFβ in vivo, fibre cells were atypical in that their nuclei did not undergo degradation; nucleated cells were commonly observed subjacent to the posterior lens capsule and also in the lens cortex (FIGS. 5B and 5D). These nucleated fibre cells were often swollen and in some areas appeared to be degenerating into large homogenous regions (FIG. 5D). Changes such as those reported in FIGS. 5B and 5D are typical of abnormalities observed in human posterior subcapsular cataract and cortical cataract.

EXAMPLE 4

Ovariectomised rat model: effect on TGFβ-induced cataract of administering equilin, coumestrol or 6-hydroxyquinoline directly to the lens Method Female Wistar rats (12–14 weeks old) were ovariectomised as described in Example 1. Equilin was obtained from Sigma, coumestrol from Apin Chemicals (Abingdon, Oxon, UK) and 6-hydroxyquinoline from Aldrich (Milwaukee, Wis., USA). Five to eleven weeks post-ovariectomy, lenses were removed and placed in 5 ml culture medium (phenol-red free minimal essential medium with antibiotics as in Example 2). Lenses were precultured for 2 days after the addition of test substances (5 μl in ethanol) to give the following final concentrations: equilin, $10^{-9}$ M; coumestrol, $10^{-6}$ M; and 6-hydroxyquinoline, $5\times10^{-7}$ M. Controls received 5 μl ethanol only. Medium was then replaced, with or without test substance as before, and TGFβ2 (0.75 ng/ml) was added to most dishes; some were cultured without addition of TGFβ to serve as controls. Medium was renewed every two days throughout the culture period without re-addition of TGFβ or test substance. Lenses were monitored daily for opacification and photographed on day 7 and the micrographs were used to determine the number of discrete opacities in each lens. Statistical analysis was carried out using Statistix software.

Results

Lenses precultured without test substance prior to exposure to TGFβ developed extensive regions of cloudiness and numerous discrete opacities appeared by the end of the culture period. The test substances significantly reduced the number of opacities induced by TGFβ under these conditions (Table 5); generalised clouding was observed in only one lens (in the equilin-treated group). Control lenses cultured without addition of TGFβ, after preculture with or without test substance, remained transparent throughout the culture period. Thus, equilin (a steroidal estrogen), coumestrol (a phytoestrogen), and 6-hydroxyquinoline (a quinoline derivative) all protected the lens against the cataractogenic effects of TGFβ under these conditions.

TABLE 5

TGFβ-induced opacification in lenses from ovariectomised rats treated with equilin, coumestrol and 6-hydroxyquinilone in vitro

| Treatment | n | No. of opacities |
|---|---|---|
| None | 10 | 7.4 ± 1.1 |
| Equilin | 8 | 3.3 ± 1.2* |
| Coumestrol | 8 | 2.0 ± 0.4** |
| 6-OH quinoline | 8 | 2.1 ± 0.5** |

Lenses were precultured for 2 days with the test substance then cultured with 0.75 ng/ml TGFβ2 plus test substance for a further 7 days. Values represent the mean ± SEM of determinations of 8–10 individual lenses. All test substances significantly reduced the number of opacities per lens: *p < 0.05; **p < 0.01, Kruskal-Wallis one-way non-parametric ANOVA.

EXAMPLE 5

Immature rat model: effect on TGFβ-induced cataract of administering tamoxifen and nafoxidene in vivo.

Method

Immature female Wistar rats (26–27 days old) were injected subcutaneously for 3 days with vehicle alone (benzyl alcohol/peanut oil, as in Example 1) or with test substance at the following doses per day: tamoxifen, 75 μg; nafoxidene, 500 μg (both from Sigma). The following day, rats were sacrificed and lenses were removed and cultured with TGFβ02 for 5 days, as described in Example 4, except that only 4 ml culture medium was used. The final concentration of TGFμ2 was 0.4 ng/ml (Expt 1) or 0.75 ng/ml (Expt 2). On the last day of culture, lenses were photographed and graded according to the severity of the opacification response, as follows: grade 0, transparent lens; grade 1, small central region of clouding or opacification noted by direct observation but too faint to record photographically; grade 2, generalised cloudiness or one discrete opacity only; grade 3, two or three discrete opacities; grade 4, more than three discrete opacities. Examples of lenses corresponding to categories 1–4 are shown in FIG. 6. Statistical analysis was carried out on pooled data, using GraphPad Prism software, to determine whether the proportion of lenses showing no opacification (Grade 0) was higher for treated rats than for controls.

Results

Figure 7:
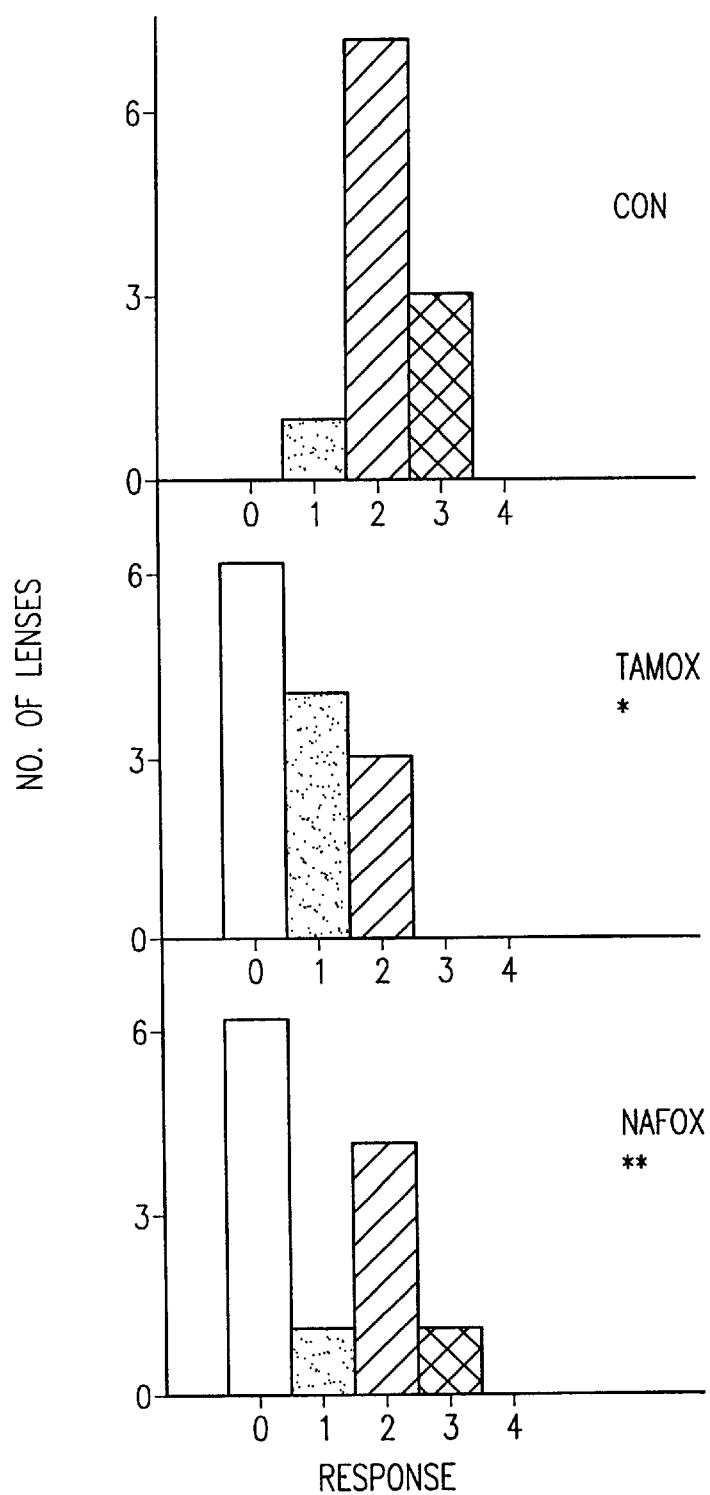
FIG. 7 shows the effect on TGFβ-induced cataract of administering tamoxifen or nafoxidene to immature female rats in vivo. Rats were injected with the test substance, or vehicle only (control), for 3 days prior to removal of the lenses, which were then cultured with 0.4–0.75 ng/ml TGFβ2 for 5 days and graded with respect to cataractous changes. Grade 0, lens remained transparent; grades 1–4, increasing severity of cataractous changes, as defined in Example 5. Data represent the pooled results of two experiments. The asterisks indicate the significance of the increase in the proportion of lenses in Grade 0 in response to treatment: *$p<0.02$;**$p<0.003$, Fisher's exact test. CON, control; TAMOX, tamoxifen; NAFOX, nafoxidene.

The results of grading the response of the lenses in each treatment group are shown in FIG. 7. Most of the lenses cultured with TGFα alone developed regions of cloudiness and most contained discrete opacities by the end of the culture period. Each of the test substances reduced the cataractogenic effect of TGFβ, as indicated by the shift in the values from right to left in the frequency distributions. All lenses were transparent on dissection and a supplementary experiment established that lenses from rats injected with tamoxifen and nafoxidene at these doses remained transparent during culture without TGFβ. Thus, tamoxifen and nafoxidene (estrogen agonist/antagonists) protected the lens against the cataractogenic effects of TGFβ under these conditions.

EXAMPLE 6

Immature rat model: effect on TGFβ-induced cataract of administering various estrogenic substances directly to the lens.

Method

Coumestrol was obtained from Apin Chemicals. Genistein, α-zearalenol and octyl phenol were obtained from Sigma. Lenses from normal 26–27-day-old female Wistar rats were placed in 4 ml culture medium (as in Example 5) and precultured after the addition of the test substance (5 μl in ethanol) at the following final concentrations: genistein, $5 \times 10^{-6}$ M; coumestrol, $10^{-6}$ M (Expt 1); genistein, $5 \times 10^{-6}$ M; coumestrol, $10^{-7}$ M (Expt 2); and α-zearalenol, $10^{-8}$ M, octyl phenol, $10^{-7}$ M (Expts 3&4) Controls received 5 μl ethanol only. The preculture period was 1 day (Expts 1,2&3) or 2 days (Expt 4). Medium was then replaced, with or without test substance as before, and TGFβ02 was added (0.75 ng/ml, Expts 1&2; 0.4 ng/ml, Expts 3&4). Representative lenses from each treatment group were processed in this way without the addition of TGFβ to assess the effects of the test substances alone. Medium was renewed every two days throughout the culture period without re-addition of TGFβ or test substance. Lenses were cultured for 5 days and photographed and graded as in Example 5. Statistical analysis was carried out on pooled data, using GraphPad Prism software, to determine whether the proportion of lenses showing little or no opacification (Grades 0–1) was higher for treated rats than for controls.

Results

Figure 8A:
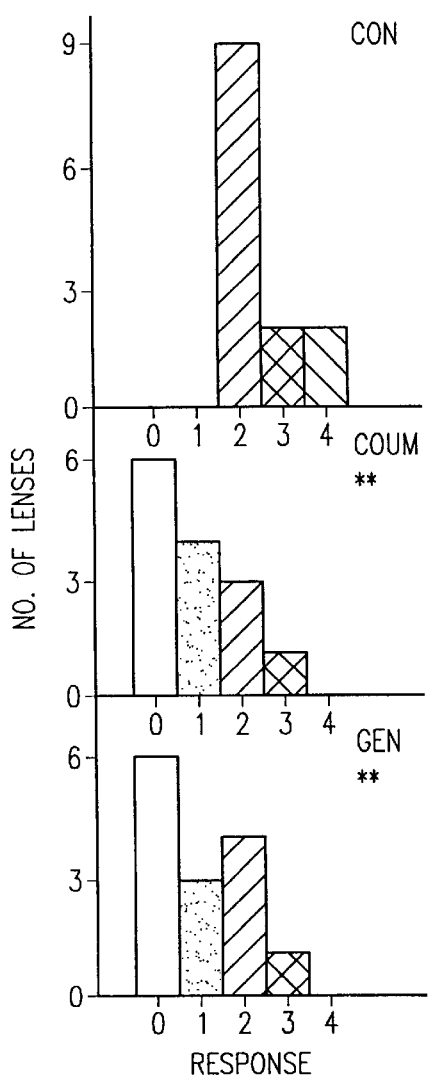
FIG. 8 shows the effect on TGFβ-induced cataract of administering (A) coumestrol or genistein and (B) α-zearalenol or octyl phenol to lenses obtained from immature female rats in vitro. Lenses were precultured for 1–2 days with the test substance, or without test substance (controls), prior to replacement of medium (including test substance) and addition of 0.4–0.75 ng/ml TGFβ02. After a further 5 days culture, lenses were graded with respect to cataractous changes. Grade 0, lens remained transparent; grades 1–4, increasing severity of cataractous changes, as defined in Example 5. Data from two experiments have been pooled in each case. The asterisks indicate the significance of the increase in the proportion of lenses in Grade 0–1 in response to treatment: *$p<0.03$; **$p<0.001$, Fisher's exact test. CON, control; COUM, coumestrol; GEN, genistein; α-ZEAR, α-zearalenol; OCT-PHE, octyl phenol.
Figure 8B:
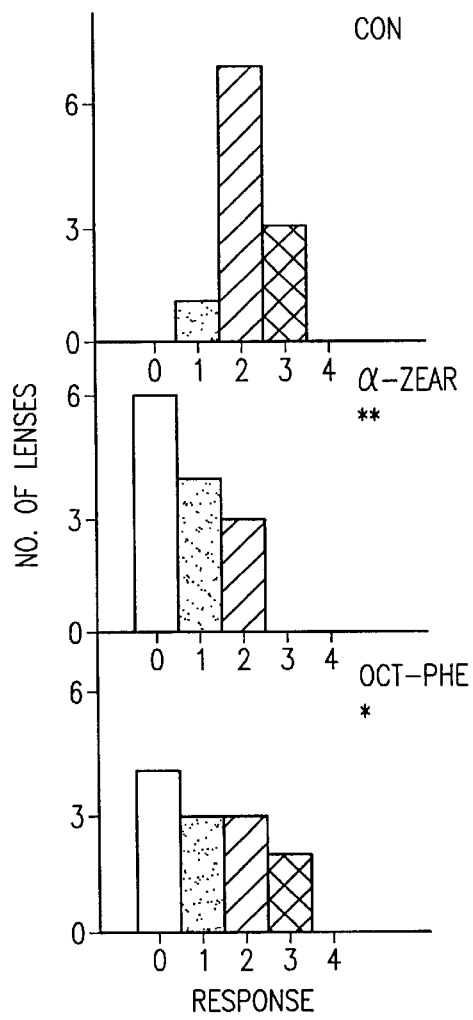

The results of grading the response of the lenses in each treatment group are shown in FIG. 8. All the lenses cultured with TGFβ alone developed regions of cloudiness and most contained numerous discrete opacities by the end of the culture period. Each of the test substances reduced the cataractogenic effect of TGFβ, as indicated by the shift in the values from right to left in the frequency distributions (FIG. 8). Control lenses cultured without addition of TGFP, after preculture with or without test substance, remained transparent throughout the culture period. Thus, coumestrol (a coumestan phytoestrogen), genistein (an isoflavone phytoestrogen), α-zearalenol (a mycoestrogen), and octyl phenol (an alkyl phenol) all protected the lens against the cataractogenic effects of TGFβ under these conditions.

Industrial Applicability

It should be clear that the methods of treatment, formulations and lens implants of the present invention will find wide use in the medical and veterinary field.

The foregoing describes only some embodiments of the present invention and modifications obvious to those skilled in the art can be made thereto without departing from the scope of the invention.

REFERENCES

1. Bisaria, K. K. 1980. The effect of estrogen on lens epithelium in the albino rat. *Ind. J. Physiol. Pharmac.* 24:357–360.
2. Black, H. 1996. Viscoelastics can be divided into two groups according to specific characteristics. *Ocular Surgery News,* International Edition 7(11):17.
3. de Iongh, R. U., C. Gordon-Thomson, A. M. Hales, C. G. Chamberlain, J. W. McAvoy. 1997. Expression patterns of TGFβ1-3 and their relative potencies for cataractogenesis. Invest. *Ophthalmol. Vis. Sci.* In Press.
4. Dorrington, J. H., J. J. Bendell and S. A. Khan. 1993. Interactions between FSH, estradiol-17 beta and transforming growth factor-beta regulate growth and differentiation in the rat gonad. *J. Steroid Biochem. Mol. Biol.* 44;441–447.

5. Eshagian, J, 1982. Human posterior subcapsular cataracts. *Trans. Ophthal. Soc. UK.* 102:364–368.
6. Green, W. R., and P. J. McDonnell. 1985. Opacification of the posterior capsule. *Trans. Ophthalmol. Soc. UK.* 104:727–739.
7. Griffing, G. T., and S. H. Allen. 1994. Estrogen replacement therapy at menopause. *Postgrad. Med.* 96:131–140.
8. Hales, A. M., M. W. Schulz, C. G. Chamberlain, and J. W. McAvoy. 1994. TGFβ1 induces lens cells to accumulate α-smooth muscle actin, a marker for subcapsular cataracts. *Curr. Eye Res.* 13:885–890.
9. Hales, A. M., C. G. Chamberlain, and J. W. McAvoy, 1995. Cataract induction in lenses cultured with transforming growth factor-β. *Invest. Ophthalmol. Vis. Sci.* 36:1709–1713.
10. Herman, M. E., and B. S. Katzenellenbogen. 1994. Alterations in transforming growth factor-alpha and -beta production and cell responsiveness during the progression of MCF-7 human breast cancer cells to estrogen-autonomous growth. *Cancer Research* 54:5867–74.
11. Jordan, V. C., S. Mittal, B. Gosden, R. Koch and M. E. Lieberman. 1985. Structure-activity relationships of estrogen. *Env. Health Per.* 61, 97–110.
12. Kappelhof, J. P. and G. F. J. M. Vrensen. 1992. The pathology of after-cataract. A minireview. *Acta Ophtalmol. Suppl* 205:13–24.
13. Kingsley, D. M. 1994. The TGF-β superfamily: new members, new receptors, and new genetic tests of function in different organisms. *Genes & Development* 8:133–146.
14. Klein, B. E. K., R Klein, K. L. P. Linton. 1992. Prevalence of age-related lens opacities in a population. The Beaver Dam Eye Study. *Ophthalmol.* 99:546–552.
15. Klein, B. E. K. 1993. Lens opacities in women in Beaver Dam, Wis.: is there evidence of an effect of sex hormones? *Trans. Am. Ophthal. Soc.* 91:517–544.
16. Lambert, B. W. 1968. The effects of progestins and estrogens on the permeability of the lens. *Arch Ophthal.* 80:230–234.
17. Liu, J., A. M. Hales, C. G. Chamberlain, and J. W. McAvoy. 1994. Induction of cataract-like changes in rat lens epithelial explants by transforming growth factor-β. *Invest. Ophthalmol. Vis. Sci.* 35:388–401.
18. Lobo, R. A. 1987. Absorption and metabolic effects of different types of estrogens and progestogens. *Obstetrics and Gynecology Clinics of North America.* 14(1):143–167.
19. Murphy, C. R., and A. W. Rogers. 1981. Effect of ovarian hormones on cell membranes in the rat uterus III the surface carbohydrates at the apex of the luminal epithelium. *Cell Biophys.* 3:305–320.
20. Ni, N. and J. D. Yager. 1994. Comitogenic effects of estrogens on DNA synthesis induced by various growth factors in cultured female rat hepatocytes. *Hepatology* 19:183–92.
21. Pastorcic, M., A. De, N. Boyadjieve, W. Vale and D. K. Sarkar. 1995. Reduction in the expression and action of transforming growth factor beta 1 on lactotropes during estrogen-induced tumorigenesis in the anterior pituitary. *Cancer Research* 55:4892–8.
22. Raisz, L. G. 1996. Estrogen and bone: new pieces to the puzzle. *Nature. Med.* 2(10)1077–8.
23. Schwab, I. R., M. A. Armstrong, G. D. Frienman, I. G. Wong, A. C. Carpantieri and C. R. Dawson. 1988. Cataract extraction. Risk factors in a health maintenance organization population under 60 years of age. *Arch Ophthalmol.* 106:1062–1065.
24. Starka, L., R. Hampl, M. Bicikova, and J. Obenberger. 1976. Identification and radioimmunologic estimation of sexual steroid hormones in aqueous humor and vitreous of rabbit eye. *Albrecht v. Graefes Arch. Klin. Exp. Ophthal.* 199:261–266.
25. Tripathi, R. C. and B. J. Tripathi. 1983. Lens morphology, aging, and cataract. *J.Gerontol.* 38:258–270.
26. Worgul, B. V. 1982. Lens. *In Ocular Anatomy, Embryology and Teratology.* F. A. Jakobiec, editor. Harper and Row, Philadelphia. 355–389.

What is claimed is:

1. A method of preventing or treating TGFβ-induced cataract or cataract-like disorders in the eye of a mammalian subject which comprises administering to the subject an effective amount of estrogen.

2. A method according to claim 1, wherein the estrogen is administered directly to or near the eye of the subject.

3. A method according to any one of claims 1 or 2, wherein the mammalian subject is a human.

4. A method according to any one of claims 1 to 3, wherein the estrogen is a steroidal estrogen.

5. A method according to any one of claims 1 to 3, wherein the estrogen is selected from the group consisting of quinolines and fused quinolines that act as steroid receptor modulators, phytoestrogens, mycoestrogens and estrogen receptor agonists/antagonists and therapeutically effective derivatives, precursors and metabolites thereof.

6. A method according to claim 5, wherein the phytoestrogen is selected from isoflavones, flavones and coumestans and therapeutically effective derivatives, precursors and metabolites thereof.

7. A method according to any one of claims 1 to 6, wherein the TGFβ-induced cataract is anterior subcapsular cataract, posterior subcapsular cataract, cortical cataract or aftercataract.

8. A pharmaceutical composition adapted for administration to the eye comprising estrogen in an ophthalmologically acceptable carrier but excluding conventional pharmaceutically acceptable carriers.

9. A pharmaceutical composition according to claim 8, wherein the estrogen is a steroidal estrogen.

10. A pharmaceutical composition according to claim 8, wherein the estrogen is selected from the group consisting of quinolines and fused quinolines that act as steroid receptor modulators, phytoestrogens, mycoestrogens and estrogen receptor agonist/antagonists and therapeutically effective derivatives, precursors and metabolites thereof.

11. A pharmaceutical composition according to claim 10, wherein the phytoestrogen is selected from isoflavones, flavones and coumestans and therapeutically effective derivatives, precursors and metabolites thereof.

12. A membranous ocular patch impregnated with estrogen.

13. A membranous ocular patch according to claim 12, wherein the estrogen is a steroidal estrogen.

14. A membranous ocular patch according to claim 12, wherein the estrogen is selected from the group consisting of quinolines and fused quinolines that act as steroid receptor modulators, phytoestrogens, mycoestrogens and estrogen receptor agonist/antagonists and therapeutically effective derivatives, precursors and metabolites thereof.

15. A membranous ocular patch according to claim 14, wherein the phytoestrogen is selected from isoflavones, flavones and coumestans and therapeutically effective derivatives, precursors and metabolites thereof.

16. A method of preventing or treating aftercataract formation in the eye of a mammalian subject following lens implant surgery which comprises implanting in the eye of the subject, a lens or lens implant coated or impregnated with estrogen.

17. A method according to claim 16, wherein the estrogen is a steroidal estrogen.

18. A method according to claim 16, wherein the estrogen is selected from the group consisting of quinolines and fused quinolines that act as steroid receptor modulators, phytoestrogens, mycoestrogens and estrogen receptor agonist/antagonists and therapeutically effective derivatives, precursors and metabolites thereof.

19. A method according to claim 18, wherein the phytoestrogen is selected from isoflavones, flavones and coumestans and therapeutically effective derivatives, precursors and metabolites thereof.

20. A lens implant coated or impregnated with estrogen.

21. A lens implant according to claim 20, wherein the estrogen is a steroidal estrogen.

22. A lens implant according to claim 20, wherein the estrogen is selected from the group consisting of quinolines and fused quinolines that act as steroid receptor modulators, phytoestrogens, mycoestrogens and estrogen receptor agonist/antagonists and therapeutically effective derivatives, precursors and metabolites thereof.

23. A lens implant according to claim 22, wherein the phytoestrogen is selected from isoflavones, flavones and coumestans and therapeutically effective derivatives, precursors and metabolites thereof.

* * * * *